United States Patent [19]

Sarges

[11] 4,130,714

[45] * Dec. 19, 1978

[54] HYDANTOIN THERAPEUTIC AGENTS

[75] Inventor: Reinhard Sarges, Mystic, Conn.

[73] Assignee: Pfizer Inc., New York, N.Y.

[ * ] Notice: The portion of the term of this patent subsequent to Oct. 3, 1995, has been disclaimed.

[21] Appl. No.: 799,586

[22] Filed: May 23, 1977

[51] Int. Cl.$^2$ .................. C07D 491/10; C07D 495/10
[52] U.S. Cl. .................................. 548/309; 424/273 R
[58] Field of Search ......................... 548/309; 424/273

[56] References Cited

U.S. PATENT DOCUMENTS 2,683,718  7/1954  Dornfeld et al. .................... 548/309

FOREIGN PATENT DOCUMENTS 1135915  6/1961  Fed. Rep. of Germany ........... 548/309

OTHER PUBLICATIONS

Arnold et al. Chem. Abst. 1963, vol. 58, cols. 3439-3440.
Boehme et al. Chem. Abst. 1974, vol. 80, No. 108305u.
Karrer et al. Organic Chemistry 2nd English ed. pp. 93-99, N.Y., Elsevier, 1946.

Primary Examiner—Natalie Trousof
Attorney, Agent, or Firm—Connolly and Hutz

[57] ABSTRACT

Several novel dextrotatory spiro-hydantoin compounds have been obtained by resolving the corresponding dl-compounds which are initially synthesized by first condensing the appropriate carbonyl ring compound, such as the corresponding 4-chromanone or thiochroman-4-one, as the case may be, with potassium cyanide and ammonium carbonate. The resulting optically-active hydantoin derivatives, such as d-6-fluoro-spiro-[chroman-4,4'-imidazolidine]-2',5'-dione and d-6'-fluoro-spiro-[imidazolidine-4,4'-thiochroman]-2,5-dione, are particularly useful in preventing or alleviating chronic diabetic complications.

5 Claims, No Drawings

HYDANTOIN THERAPEUTIC AGENTS

BACKGROUND OF THE INVENTION

This invention relates to new and useful optically-active hydantoin derivatives in the field of medicinal chemistry. More particularly, it is concerned with certain novel dextrorotatory spiro-hydantoin compounds, which are of especial value in view of their ability to effectively control certain chronic complications arising from diabetes mellitus (e.g., diabetic cataracts and neuropathy). The invention also includes a new method of therapy within its scope.

In the past, various attempts have been made by numerous investigators in the field of organic medicinal chemistry to obtain new and better oral antidiabetic agents. For the most part, these efforts have involved the synthesis and testing of various heretofore new and unavailable organic compounds, particularly in the area of the sulfonylureas, in an endeavor to determine their ability to lower blood sugar (i.e., glucose) levels to a substantially high degree when given by the oral route of administration. However, in the search for newer and still more effective antidiabetic agents, little is known about the effect of other organic compounds in preventing or arresting certain chronic complications of diabetes, such as diabetic cataracts, neuropathy and retinopathy, etc. Nevertheless, K. Sestanj et al. in U.S. Pat. No. 3,821,383 do disclose that certain aldose reductase inhibitors like 1,3-dioxo-1H-benz[d,e]-isoquinoline-2(3H)-acetic acid and some closely-related derivatives thereof are useful for these purposes even though these particular compounds are not known to be hypoglycemic per se. These particular aldose reductase inhibitors all function by inhibiting the activity of the enzyme aldose reductase, which is primarily responsible for regulating the reduction of aldoses (like glucose and galactose) to the corresponding polyols (such as sorbitol and galactitol) in the human body. In this way, unwanted accumulations of galactitol in the lens of galactosemic subjects and of sorbitol in the lens, peripheral nervous cord and kidney of various diabetic subjects are thereby prevented or otherwise reduced as the case may be. As a result, these compounds are definitely of value as aldose reductase inhibitors for controlling certain chronic diabetic complications, including those of an ocular nature, since it is already known in the art that the presence of polyols in the lens of the eye invariably leads to cataract formation together with a concomitant loss of lens clarity.

SUMMARY OF THE INVENTION

In accordance with the present invention, it has now been rather surprisingly found that certain novel dextrorotatory spiro-hydantoin compounds are extremely useful when employed in therapy as aldose reductase inhibitors for the control of chronic complications arising in a diabetic subject. These novel dextrorotatory isomers are all far more active in this respect than the corresponding dl-compounds from which they are derived, despite the fact that the same dl-, d- and l-forms are all found to be substantially equipotent as anticonvulsant agents.

More specifically, the novel compounds of this invention are all selected from the group consisting of the dextrorotatory forms of asymmetric spiro-hydantoins of the formula:

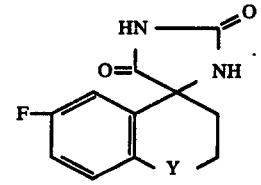

and the base salts thereof with pharmacologically acceptable cations, wherein Y is oxygen or sulfur. Typical member compounds specifically embraced by this invention include d-6-fluoro-spiro-[chroman-4,4'-imidazolidine]-2',5'-dione and d-6'-fluoro-spiro-[imidazolidine-4,4'-thiochroman]-2,5-dione, respectively. These two particular compounds are both extremely potent as regards their aldose reductase inhibitory activity, in addition to being equally effective in lowering sorbitol levels in the sciatic nerve and lens of diabetic subjects and galactitol levels in the lens of galactosemic subjects to a very significantly high degree.

DETAILED DESCRIPTION OF THE INVENTION

In accordance with the process employed for obtaining the novel dextrorotatory compounds of this invention, a corresponding racemic or dl-spiro-hydantoin having the same general structural formula as previously indicated for the optically-active compound is contacted with at least an equimolar amount of 1-brucine or a similarly optically-active alkaloid like cinchonidine in a suitable reaction-inert organic solvent preferably selected from the class consisting of lower alkanols. The resulting diastereoisomeric salts are then separated by means of fractional crystallization and the less soluble salt is converted to the desired optically-active spiro-hydantoin by means of decomposition with acid in a conventional manner.

In accordance with a more detailed consideration of the aforementioned method of resolution of this invention, the first step leading to the production of the diastereoisomers is preferably carried out in a lower alkanol solvent of from one to three carbon atoms using 1-brucine as the resolving agent of choice. In practice, it is usually preferable to employ equimolar amounts of racemic compound and resolving agent in order to minimize cost and to maximize purity of product, but a slight excess of alkaloid can be used without demonstrably affecting the outcome of the salt-formation step or the nature of the final product obtained. Needless to say, time is not critical in this connection and is necessarily dependent upon the nature of the starting materials, their concentration in solution and the actual temperatures employed. Upon completion of the salt-formation step, the desired diastereoisomer normally separates from the mixture by fractional crystallization and this usually requires a period of from about 2 to about 24 hours within a crystallization temperature range of from about −20° C. up to about 60° C. for the present purposes at hand. The diastereoisomer is then further purified by means of recrystallization, preferably using the same type alkanol solvent earlier employed in the salt-formation step, until full optical purity is achieved, i.e., as evidenced by a constant melting point and constant optical rotation for the aforesaid diastereoisomer.

Conversion of the alkaloidal salts thus obtained to the desired optically-active hydantoins is then accomplished in a most facile manner by means of decomposition with acid and preferably, by using the standard techniques of acid hydrolysis. For instance, the salt can be treated in an aqueous medium with a mineral acid such as sulfuric acid, hydrochloric acid, hydrobromic acid or hydriodic acid or with an organic acid such as a lower alkanoic acid like acetic acid or a halogenated lower alkanoic acid like β-chloropropionic acid or trichloroacetic acid. In practice, it most convenient to employ a dilute aqueous acid per se for the present purposes at hand, with sulfuric acid and hydrochloric acid generally being preferred as the acid components in this connection. In order to further facilitate the hydrolysis step, a suitable water-immiscible organic solvent such as a lower alkyl alkanoic acid ester like ethyl acetate is preferably employed in conjunction with the aforesaid dilute aqueous acidic medium, whereby the desired optically-active spiro-hydantoin compound (i.e., the dextrorotatory isomer) is conveniently extracted into the organic layer and thereafter isolated by conventional means.

The dl-spiro-hydantoin compounds used as substrates in the resolution process of this invention are all readily synthesized by first condensing an appropriate carbonyl ring compound, such as the corresponding 4-chromanone or thiochroman-4-one, of the formula:

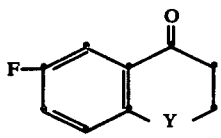

wherein Y is as previously defined, with an alkali metal cyanide (e.g., sodium cyanide or potassium cyanide) and ammonium carbonate to form the desired spiro-hydantoin final product (i.e., racemic compound) of the structural formula previously indicated. This particular reaction is normally carried out in the presence of a reaction-inert polar organic solvent medium in which both the reactants and reagents are mutually miscible. Preferred organic solvents for use in this connection include cyclic ethers such as dioxane and tetrahydrofuran, lower alkylene glycols like ethylene glycol and trimethylene glycol, water-miscible lower alkanols such as methanol, ethanol and isopropanol, as well as N,N-di(lower alkyl) lower alkanoamides like N,N-dimethylformamide, N,N-diethylformamide and N,N-dimethylacetamide, etc. In general, the reaction is conducted at a temperature that is in the range of from about 20° C. up to about 120° C. for a period of about 2 hours to about 4 days. Although the amount of reactant and reagents employed in the reaction can vary to some extent, it is preferable to employ at least a slight molar excess of the alkali metal cyanide reagent with respect to the carbonyl ring compound starting material in order to effect maximum yield. Upon completion of the reaction, the desired product is easily isolated in a conventional manner, e.g., by first diluting the reaction mixture with water (boiling if necessary) and then cooling the resultant aqueous solution to room temperature, followed by acidification to afford the particular dl-spiro-hydantoin compound in the form of a readily-recoverable precipitate.

The starting materials required for preparing the aforesaid dl-spiro-hydantoin compounds are, for the most part, known compounds which can easily be synthesized by those skilled in the art starting from common chemical reagents and using conventional methods of organic synthesis. For instance, 6-fluorothiochroman-4-one is a known compound, while 6-fluoro-4-chromanone is readily obtained by condensing β-(p-fluorophenoxy)propionic acid in the presence of polyphosphoric acid. The latter organic acid, used as starting material in this connection, is ultimately derived from a commercially available compound.

The chemical bases which are used as reagents in this invention to prepare the aforementioned pharmaceutically acceptable base salts are those which form non-toxic salts with the herein described acidic dextrorotatory spiro-hydantoin compounds, such as d-6-fluoro-spiro-[chroman-4,4'-imidazolidine]-2',5'-dione, for example. These particular non-toxic base salts are of such a nature that their cations are said to be essentially non-toxic in character over the wide range of dosage administered. Examples of such cations include those of sodium, potassium, calcium and magnesium, etc. These salts can easily be prepared by simply treating the aforementioned d-spiro-hydantoin compounds with an aqueous solution of the desired pharmacologically acceptable cation, and then evaporating the resulting solution to dryness while preferably being placed under reduced pressure. Alternatively, they may also be prepared by mixing lower alkanolic solutions of the said acidic compounds and the desired alkali metal alkoxide together, and then evaporating the resulting solution to dryness in the same manner as before. In either case, stoichiometric quantities of reagents must be employed in order to ensure completeness of reaction and maximum production of yields with respect to the desired final product.

As previously indicated, the dextrorotatory spiro-hydantoin compounds of this invention are all readily adapted to therapeutic use as aldose reductase inhibitors for the control of chronic diabetic complications, in view of their ability to reduce lens sorbitol levels in diabetic subjects to a statistically significant degree. For instance, d-6-fluoro-spiro-[chroman-4,4'-imidazolidine]-2',5'-dione, a typical and preferred agent of the present invention, has been found to consistently control (i.e., inhibit) the formation of sorbitol levels in diabetic rats to a significantly high degree when given by the oral route of administration at dose levels ranging from 0.25 mg./kg. to 5.0 kg., respectively, without showing any substantial signs of toxic side effects. The other compounds of this invention also cause similar results. Furthermore, the herein described compounds of this invention can be administered by either the oral or parenteral routes of administration, for the present purposes at hand, without causing any significant untoward pharmacological side reactions to occur in the subject to whom they are so administered. In general, these compounds are ordinarily administered in dosages ranging from about 0.05 mg. to about 5.0 mg. per kg. of body weight per day, although variations will necessarily occur depending upon the weight and condition of the subject being treated and the particular route of administration chosen.

In connection with the use of the dextrorotatory spiro-hydantoin compounds of this invention for the treatment of diabetic subjects, it is to be noted that these compounds may be administered either alone or in combination with pharmaceutically acceptable carriers by either of the routes previously indicated, and that such administration can be carried out in both single and multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for just such a purpose. In general, the therapeutically useful compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various like combinations thereof.

For purposes of parenteral administration, solutions of these particular d-spiro-hydantoins in sesame or peanut oil or in aqueous propylene glycol may be employed as well as sterile aqueous solutions of the corresponding water soluble, alkali metal or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art. Additionally, it is also possible to administer the aforesaid spiro-hydantoin compounds topically via an appropriate opthalmic solution suitable for the present purposes at hand, which can then be given dropwise to the eye.

The activity of the compounds of the present invention, as agents for the control of chronic diabetic complications, is determined by their ability to successfully pass one or more of the following standard biological and/or pharmacological tests, viz, (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse alredy-elevated sorbitol levels in the sciatic nerve and lens of chronic streptozotocin-induced diabetic rats; (4) measuring their ability to prevent or inhibit galactitol formation in the lens of acutely galactosemic rats, and (5) measuring their ability to delay cataract formation and reduce the severity of lens opacities in chronic galactosemic rats.

Preparation A

A mixture consisting of 3.5 g. (0.019 mole) of $\beta$-(p-fluorophenoxy)propionic acid [Finger et al., *Journal of the American Chemical Society*, Vol. 81, p. 94 (1959)] and 40 g. of polyphosphoric acid was heated on a steam bath for a period of 10 minutes and then poured into 300 ml. of ice-water. The resulting aqueous mixture was next extracted with three separate portions of ethyl acetate, and the combined organic layers were subsequently washed with dilute aqueous sodium bicarbonate solution and then with water, followed by drying over anhydrous magnesium sulfate. After removal of the drying agent by means of filtration and the solvent by means of evaporation under reduced pressure, there was ultimately obtained a residue that was subsequently recrystallized from ethanol to afford 2.93 g. (93%) of pure 6-fluoro-4-chromanone, m.p. 114°–116° C.

Anal. Calcd. for $C_9H_7FO_2.0.25\ H_2O$: C, 63.34; H, 4.43. Found: C, 63.24; H, 4.15.

Preparation B

A mixture consisting of 397 g. (2.39 mole) of 6-fluoro-4-chromanone (prepared as described in Preparation A), 233 g. (3.58 mole) of potassium cyanide and 917 g. (9.56 mole) of powdered ammonium carbonate in 3000 ml. of 50% aqueous ethanol was heated at 65° C. for a period of approximately 63 hours. The reaction mixture was then cooled to room temperature ($\sim$25° C.), diluted with 2000 ml. of water and thereafter acidified with 6N hydrochloric acid. The pale yellow crystals so obtained were subsequently collected by means of suction filtration, washed well with water and thereafter dissolved in 2N aqueous sodium hydroxide solution. Extraction of the latter solution with three-1000 ml. portions of ethyl acetate, followed by acidification of the basic aqueous phase with 6N hydrochloric acid then gave pale yellow crystals that were again washed with water and air dried to constant weight. After recrystallization from boiling methanol (initial volume of 9 liters was reduced to 5 liters), there was obtained pure dl-6-fluoro-spiro-[chroman-4,4'-imidazolidine]-2',5'-dione (m.p. 239°–241° C.) in a 276 g. (44%) yield. A second crop (82 g.) of crystals obtained from the filtrate increased the yield of pure material to 64%.

Preparation C

The procedure described in Preparation B was repeated except that 191 g. (1.05 mole) of 6-fluorothiochroman-4-one [*Chemical Abstracts*, Vol. 70, p. 47335x (1969)], 102 g. (1.57 mole) of potassium cyanide and 391 g. (4.08 mole) of powdered ammonium carbonate were reacted in 1000 ml. of 50% aqueous ethanol at 65° C. (using an oil bath) for a period of approximately 66 hours. The reaction mixture was then poured into 1500 ml. of water and boiled for 15 minutes in order to destroy excess ammonium carbonate. After cooling to room temperature, it was acidified with concentrated hydrochloric acid and then worked-up in the same manner as described for the corresponding mixture in Preparation B. In this way, there was ultimately obtained 224 g. (85%) of pure dl-6'-fluoro-spiro-[imidazolidine-4,4'-thiochroman]-2,5-dione (m.p. 200°–202° C.) without any recrystallization step being necessary.

EXAMPLE I

A solution consisting of 120 g. (0.508 mole) of dl-6-fluoro-spiro-[chroman-4,4'-imidazolidine]-2',5'-dione (m.p. 239°–241° C.) and 237 g. (0.508 mole) of l-brucine tetrahydrate dissolved in 1.8 liters of boiling ethanol was allowed to cool slowly, and the precipitated crystals (A) were subsequently collected by means of suction filtration and the resulting filtrate (B) thereafter saved. The crystals (A) consisted of the l-brucine salt of d-6-fluoro-spiro-[chroman-4,4'-imidazolidine]-2',5'-dione, isolated as the ethanolate, m.p. 114°–118° C. (decomp.) after recrystallization from ethanol.

Anal. Calcd. for $C_{11}H_9FN_2O_3 \cdot C_{23}H_{26}N_2O_4 \cdot C_2H_5OH$: C, 63.88; H, 6.12; N, 8.28. Found: C, 63.60; H, 6.07; N, 8.22.

After further recrystallization of the above crystals (A) from ethanol (1.5 liters), the aforesaid diastereoisomer was then treated with 1.0 liter of ethyl acetate and 1.0 liter of 1N aqueous hydrochloric acid. The separated organic layer was then collected, dried over anhydrous magnesium sulfate, filtered and subsequently concentrated in vacuo to afford a solid residual material. The latter residue was then crystallized from 1.0 liter of ethanol to give 45 g. of crude product, viz, the dextrorotatory isomer of 6-fluoro-spiro-[chroman-4,4'-imidazolidine]-2',5'-dione. Recrystallization of the latter material from 300 ml. of ethanol then gave 37 g. (62%) of pure d-6-fluoro-spiro-[chroman-4,4'-imidazolidine]-2',5'-dione, m.p. 241°–243° C.; $[\alpha]_D^{25°} + 54.0°$ (c = 1 in methanol).

Anal. Calcd. for $C_{11}H_9FN_2O_3$: C, 55.93; H, 3.84; N, 11.86. Found: C, 55.59; H, 3.88; N, 11.52.

The original filtrate (B) was then treated with 75 ml. of 10% aqueous hydrochloric acid and the precipitated crystals were subsequently collected in the usual manner to afford the l-brucine salt of l-6-fluoro-spiro-[chroman-4,4'-imidazolidine]-2',5'-dione, isolated as the monohydrochloride dihydrate, m.p. 172°–174° C.

Anal. Calcd. for $C_{11}H_9FN_2O_3 \cdot C_{23}H_{26}O_4 \cdot HCl \cdot 2H_2O$: C, 58.07; H, 5.73; N, 7.97. Found: C, 58.05; H, 5.79; N, 7.98.

This particular diastereoisomer (m.p. 172°–174° C.) was then treated with 1.0 liter of ethyl acetate and 600 ml. of 10% aqueous sulfuric acid and the resulting organic layer was thereafter separated, dried over anhydrous magnesium sulfate, filtered and subsequently concentrated in vacuo to afford 41 g. of the crude l-isomer. Recrystallization of the latter material from 400 ml. of ethanol then gave 34 g. (52%) of pure l-6-fluoro-spiro-[chroman-4,4'-imidazolidine]-2',5'-dione, m.p. 241°–243° C., $[\alpha]_D^{25°} - 54.8°$ (c = 1 in methanol).

Anal. Calcd. for $C_{11}H_9FN_2O_3$: C, 55.93; H, 3.84; N, 11.86. Found: C, 55.59; H, 3.89; N, 11.80.

EXAMPLE II

A solution consisting of 2.52 g. (0.01 mole) of dl-6'-fluoro-spiro-[imidazolidine-4,4'-thiochroman]-2,5-dione (m.p. 200°–202° C.) and 4.3 g. (0.01 mole) of l-brucine dihydrate dissolved in 125 ml. of boiling ethanol was allowed to cool slowly, and the precipitated crystals (A) were subsequently collected by means of suction filtration and the resulting filtrate (B) thereafter saved. The crystals (A) were then recrystallized twice from 100 ml. of ethanol to afford 2.1 g. of pure l-brucine salt of d-6'-fluoro-spiro-[imidazolidine-4,4'-thiochroman]-2,5-dione, isolated as the ethanolate, m.p. 147°–149° C.

Anal. Calcd. for $C_{11}H_9FN_2O_2S \cdot C_{23}H_{26}N_2O_4 \cdot C_2H_5OH$: C, 62.40; H, 5.97; N, 8.09. Found: C, 62.22; H, 6.23; N, 8.06.

The above crystals (A) were then shaken with 100 ml. of ethyl acetate and 200 ml. of 3N aqueous hydrochloric acid in order to convert the aforesaid diastereoisomer into the corresponding optically active hydantoin. The separated organic layer obtained in this manner was then collected, dried over anhydrous magnesium sulfate and filtered, and the resulting filtrate was subsequently concentrated in vacuo to afford a fine residual material. Recrystallization of the latter material from 20 ml. of ethanol then gave 230 mg. (18%) of pure d-6'-fluoro-spiro-[imidazolidine-4,4'-thiochroman]-2,5-dione, m.p. 224°–226° C., $[\alpha]_D^{25°} + 71.8°$ (c = 1 in methanol).

Anal. Calcd. for $C_{11}H_9FN_2O_2S$: C, 52.37; H, 3.60; N, 11.11. Found: C, 52.19; H, 3.44; N, 10.94.

The original filtrate (B) was then concentrated in vacuo and the resulting crystalline residue was subsequently recrystallized from 50 ml. of ethanol to afford 1.6 g. of crystals consisting of the pure l-brucine salt of l-6'-fluoro-spiro-[imidazolidine-4,4'-thiochroman]-2,5-dione, isolated as the ethanolate, m.p. 120°–124° C.

Anal. Calcd. for $C_{11}H_9FN_2O_2S \cdot C_{23}H_{26}N_2O_4 \cdot C_2H_5OH$: C, 62.40; H, 5.97; N, 8.09. Found: C, 62.21; H, 5.94; N, 8.09.

This particular diastereoisomer (m.p. 120°–124° C.) was then shaken with 100 ml. of ethyl acetate and 200 ml. of 1N aqueous hydrochloric acid, and the resulting organic layer was thereafter separated, dried over anhydrous magnesium sulfate, filtered and subsequently evaporated to dryness while under reduced pressure. The residue (190 mg.) was then recrystallized from 10 ml. of ethanol and finally from ethyl acetate/n-hexane to afford 64 mg. (5.8%) of pure l-6'-fluoro-spiro-[imidazolidine-4,4'-thiochroman]-2,5-dione, m.p. 223°–225° C.; $[\alpha]_D^{25°} - 73.8°$ (c = 1 in methanol).

Anal. Calcd. for $C_{11}H_9FN_2O_2S$: C, 52.37; H, 3.60; N, 11.11. Found: C, 52.37; H, 3.66; N, 11.00.

EXAMPLE III

The sodium salt of d-6-fluoro-spiro-[chroman-4,4'-imidazolidine]-2',5'-dione (the product of Example I) is prepared by dissolving said compound in water containing an equivalent amount in moles of sodium hydroxide and then freeze-drying the mixture. In this way, the desired alkali metal salt of the hydantoin is obtained in the form of an amorphous powder which is freely soluble in water.

In like manner, the potassium and lithium salts are also similarly prepared, as are all the alkali metal salts of d-6'-fluoro-spiro-[imidazolidine-4,4'-thiochroman]-2,5-dione (the product of Example II).

EXAMPLE IV

The calcium salt of d-6'-fluoro-spiro-[imidazolidine-4,4'-thiochroman]-2,5-dione (the product of Example II) is prepared by dissolving said compound in water containing an equivalent amount in moles of calcium hydroxide and then freeze-drying the mixture. The corresponding magnesium salt is also prepared in this manner, as are all the other alkaline-earth metal salts not only of this particular compound, but also of d-6-fluoro-spiro-[chroman-4,4'-imidazolidine]-2',5'-dione (the product of Example I).

EXAMPLE V

A dry solid pharmaceutical composition is prepared by blending the following materials together in the proportions by weight specified below;

| | |
|---|---|
| d-6-Fluoro-spiro-[chroman-4,4'-imidazolidine]-2',5'-dione | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 200 mg. of the active ingredient. Other tablets are also prepared in a similar fashion containing 25, 50 and 100 mg. of the active ingredient, respectively, by merely using the appropriate amount of the hydantoin compound in each case.

EXAMPLE VI

A dry solid pharmaceutical composition is prepared by combining the following materials together in the proportions by weight indicated below:

| | |
|---|---|
| d-6'-Fluoro-[imidazolidine-4,4'-thiochroman]-2,5-dione | 50 |
| Calcium carbonate | 20 |
| Polyethylene glycol, average molecular weight 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE VII

The following spiro-hydantoin compounds of Preparations B and C and Examples I-II, respectively, were tested for their ability to reduce or inhibit aldose reductase enzyme activity via the procedure of S. Hayman et al., as described in the *Journal of Biological Chemistry*, Vol. 240, p. 877 (1965) and as modified by K. Sestanj et al. in U.S. Pat. No. 3,821,383. In every case, the substrate employed was partially purified aldose reductase enzyme obtained from calf lens. The results obtained with each compound are expressed below in terms of percent inhibition of enzyme activity with respect to the various concentration levels tested:

| Compound | Percent Inhibition (%) | | | |
|---|---|---|---|---|
| | $10^{-4}$M | $10^{-5}$M | $10^{-6}$M | $10^{-7}$M |
| dl-Cpd. of Prep. B | 85 | 58 | 52 | 3 |
| d-Isomer of Ex. I | 100 | 100 | 98 | 39 |
| l-Isomer of Ex. I | 88 | 63 | 23 | −4 |
| dl-Cpd. of Prep. C | 81 | 77 | 66 | 38 |
| d-Isomer of Ex. II | 89 | 80 | 76 | 74 |
| l-Isomer of Ex. II | 87 | 65 | 11 | 10 |

EXAMPLE VIII

The following spiro-hydantoin compounds of Preparations B and C and Examples I-II, respectively, were tested for their ability to reduce or inhibit sorbitol accumulation in the sciatic nerve of streptozotocinized (i.e., diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose levels indicated 4, 8 and 24 hours following the administration of streptozotocin. The results obtained in this manner are presented below in terms of percent inhibition (%) afforded by the test compound as compared to the case where no compound was administered (i.e., the untreated animal where sorbitol levels normally rise from approximately 50–100 mM/g. tissue to as high as 400 mM/g. tissue in the 27-hour test period):

| Compound | Percent Inhibition (%) | | | | |
|---|---|---|---|---|---|
| | 0.25 | 0.75 | 1.5 | 2.5 | 5.0 mg./kg. |
| dl-Cpd. of Prep. B | 19 | 45 | 72 | — | — |
| d-Isomer of Ex. I | 47 | 78 | — | — | — |
| l-Isomer of Ex. I | — | 19 | — | 6 | 22 |
| dl-Cpd. of Prep. C | — | 13 | 45 | 74 | — |
| d-Isomer of Ex. II | — | 55 | — | — | — |

What is claimed is:

1. A compound selected from the group consisting of the dextrorotatory isomers of asymmetric spiro-hydantoins of the formula:

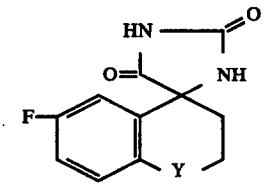

and the base salts thereof with pharmacologically acceptable cations, wherein Y is oxygen or sulfur.

2. A compound as claimed in claim 1 wherein Y is oxygen.
3. A compound as claimed in claim 1 wherein Y is sulfur.
4. d-6-Fluoro-spiro-[chroman-4,4'-imidazolidine]-2',5'-dione.
5. d-6'-Fluoro-spiro[imidazolidine-4,4'-thiochroman]-2,5-dione.

* * * * *